United States Patent
Trapp et al.

[11] Patent Number: 6,126,666
[45] Date of Patent: Oct. 3, 2000

[54] DEVICE FOR INSERTING A SURGICAL SUTURE NEEDLE INTO AN ENDOSCOPIC SUTURE APPARATUS

[75] Inventors: Rainer Trapp, Graben-Neudorf; Helmut Wurster, Oberderdingen, both of Germany

[73] Assignee: Forschungszcutrum Karlsruhe GmbH, Karlsruhe, Germany

[21] Appl. No.: 09/379,370

[22] Filed: Aug. 23, 1999

Related U.S. Application Data

[63] Continuation-in-part of application No. PCT/EP98/01468, Mar. 13, 1998.

[30] Foreign Application Priority Data

Apr. 14, 1997 [DE] Germany .................. 197 15 387

[51] Int. Cl.⁷ .................. A61B 17/04; B65D 85/24
[52] U.S. Cl. .................. 606/144; 206/339; 206/340; 206/341
[58] Field of Search .................. 606/139, 144; 206/63.3, 339, 340, 341; 221/191

[56] References Cited

U.S. PATENT DOCUMENTS

| | | |
|---|---|---|
| 4,183,431 | 1/1980 | Schmidt et al. .................. 206/63.3 |
| 4,424,898 | 1/1984 | Thyen et al. .................. 206/63.3 |
| 5,078,730 | 1/1992 | Li et al. .................. 606/228 |
| 5,086,914 | 2/1992 | Mish et al. .................. 206/63.3 |
| 5,226,536 | 7/1993 | Elliott .................. 206/369 |
| 5,271,495 | 12/1993 | Alpern .................. 206/63.3 |
| 5,478,344 | 12/1995 | Stone et al. .................. 606/144 |
| 5,478,345 | 12/1995 | Stone et al. .................. 606/144 |
| 5,591,181 | 1/1997 | Stone et al. .................. 606/144 |
| 5,630,825 | 5/1997 | De La Torre et al. .................. 206/339 |
| 5,728,107 | 3/1998 | Zlock et al. .................. 606/139 |
| 5,733,293 | 3/1998 | Scirica et al. .................. 206/339 |
| 5,741,300 | 4/1998 | Li .................. 606/232 |
| 5,908,428 | 6/1999 | Scirica et al. .................. 606/139 |

*Primary Examiner*—Gary Jackson
*Attorney, Agent, or Firm*—Klaus J. Bach

[57] ABSTRACT

In a device for inserting a surgical suture needle into an endoscopic suture apparatus wherein the device includes two legs which are movable relative to each other, one of the legs has a front end with means for receiving a jaw of an endoscopic suturing apparatus and the other leg has needle engagement means for holding a surgical needle in a predetermined position such that one needle tip enters a needle support of the surgical suturing apparatus jaw when the other leg holding the needle is moved toward the one leg while the one leg is disposed on the surgical suturing apparatus jaw.

15 Claims, 5 Drawing Sheets

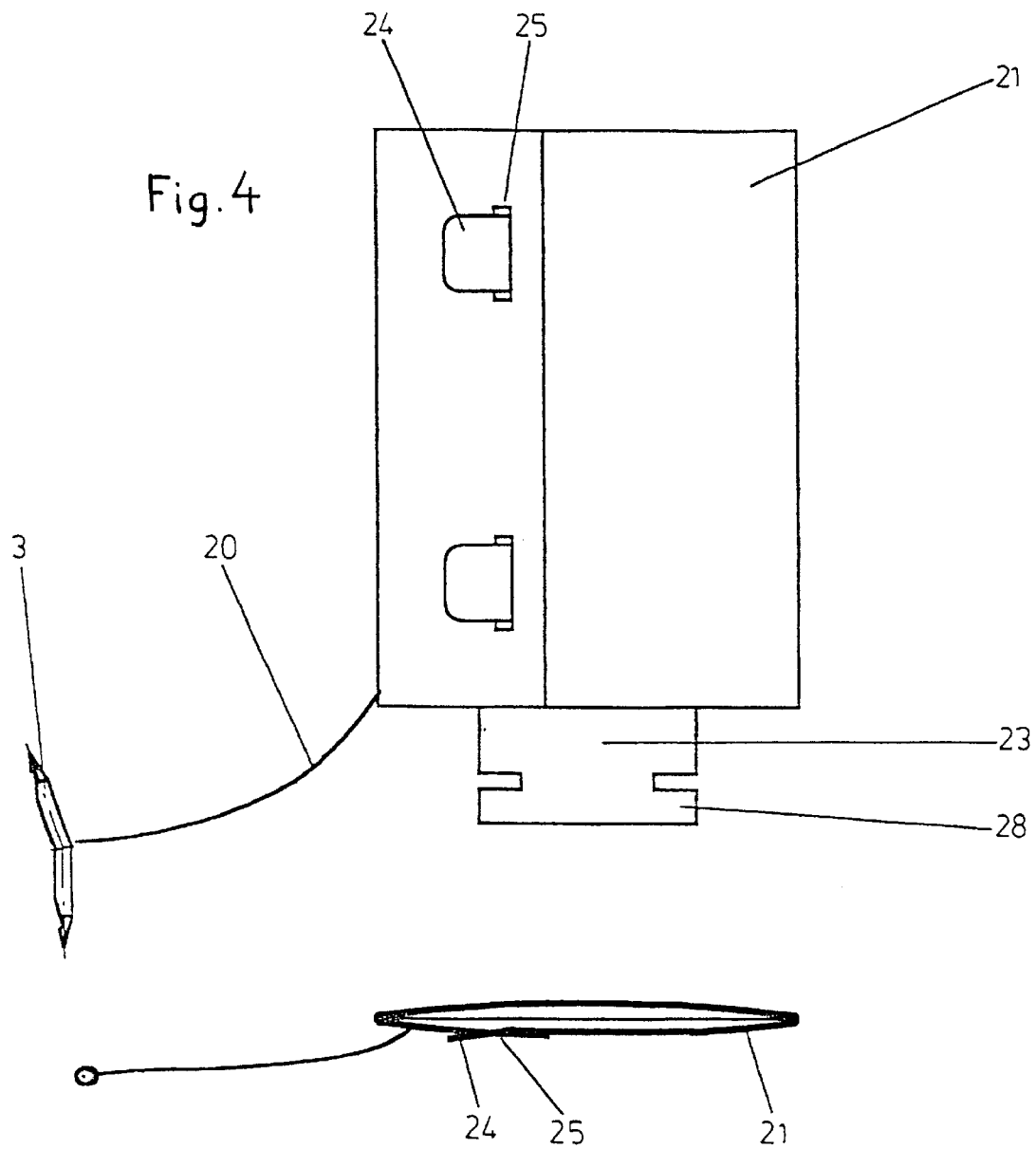
Fig. 4
Fig. 5a
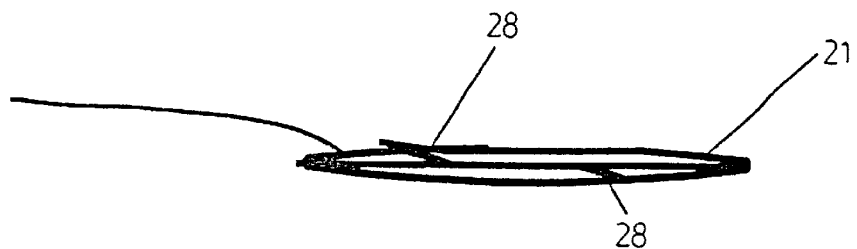
Fig. 5b

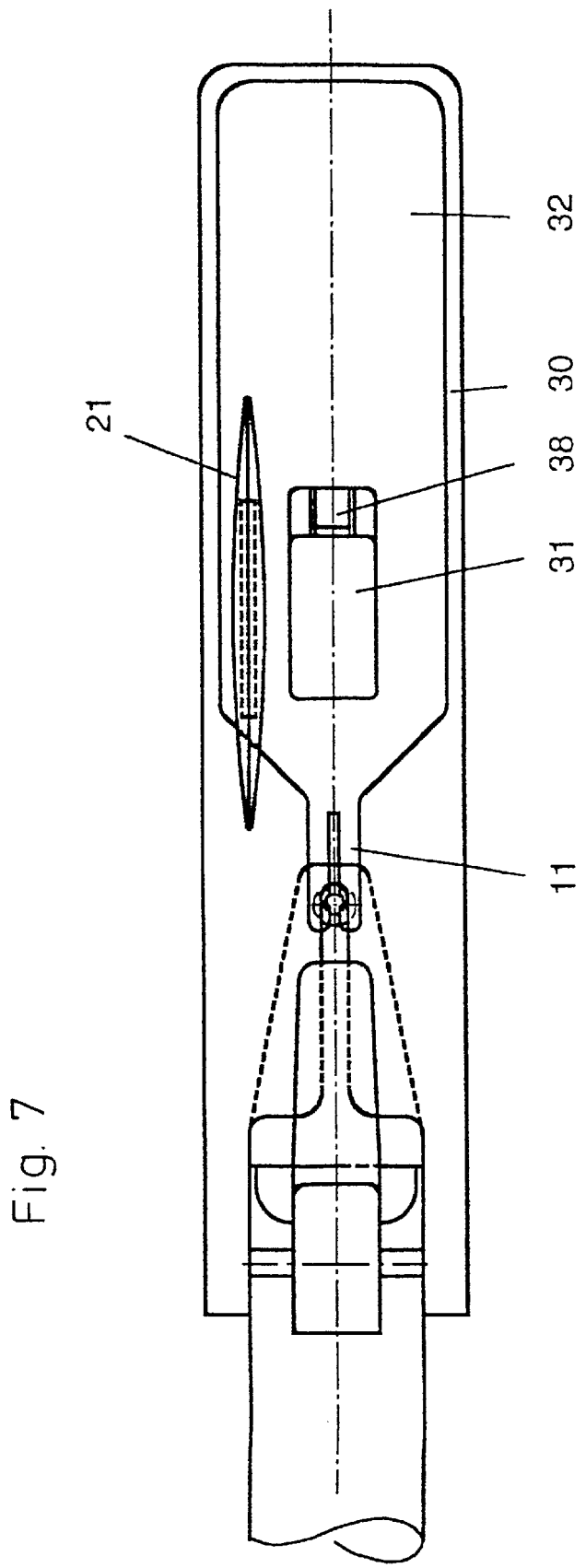

DEVICE FOR INSERTING A SURGICAL SUTURE NEEDLE INTO AN ENDOSCOPIC SUTURE APPARATUS

This is a continuation in part application of international patent application PCT/EP98/01468 filed Mar. 13, 1998 and designating the US and claiming the priority of German patent application 197 15 387.9 filed Apr. 14, 1997.

BACKGROUND OF THE INVENTION

The invention resides in a device for inserting a surgical suture needle into a suture apparatus particularly an endoscopic suture apparatus.

DE 41 24 383 and DE 44 23 881 disclose surgical suture apparatus, wherein a needle installed in the apparatus is moved back and forth between two jaws. However, the insertion of the usually very small needle, which is often only 10 mm long, is problematic. Insertion of the needle by hand is unsafe and, furthermore, may result in injuries.

Manufacturers of medical-technical products often distribute, together with suturing apparatus, magazines, which contain surgical needles that are already threaded and from which the needles together with the thread can be removed one after the other. The problem of attaching the magazine to the suturing apparatus in such a way that the needles can be reliably removed and transferred however is not solved satisfactorily, so that the procedure may easily fail.

It is the object of the present invention to provide a device, which facilitates the insertion of surgical needles taken from a magazine into a surgical suturing apparatus, which is used for endoscopic surgery. The device is to safely guide the needle into a proper position for installation in the suturing apparatus.

SUMMARY OF THE INVENTION

In a device for inserting a surgical suture needle into an endoscopic suture apparatus wherein the device includes two legs which are movable relative to each other, one of the legs has a front end with means for receiving a jaw of an endoscopic suturing apparatus and the other leg has needle engagement means for holding a surgical needle in a predetermined position such that one needle tip enters a needle support of the surgical suturing apparatus jaw when the other leg holding the needle is moved toward the one leg while the one leg is disposed on the surgical suturing apparatus jaw.

Essentially, the needle, which is to be inserted into the suturing apparatus and which often is already provided with a thread is held in a device which is placed onto the head of the suturing apparatus, where it is engaged in a predetermined position. By compression of the two legs of the needle insertion device, the needle is introduced accurately into one of the two needle supports of the suturing apparatus and is then fixed in position by closing of the jaws of the suturing device and actuating a locking switch. Then the insertion device is removed. The surgical needle with the thread already in place is thus properly installed in the suturing apparatus.

It is advantageous if, during installation of the needle, the needle is movable, when held in the insertion device, about the pivot point of the jaws of the suturing apparatus. In this way the installation of the needle into the needle supports of the jaws of the suturing apparatus is as accurate as possible. The movable part of the insertion device, which holds the needle, also supports the packaging of the needle or the needle magazine together with the thread. Upon removal of the needle insertion device from the suturing apparatus, the thread, which his attached to the needle, is pulled out of the packaging. Then the suturing apparatus is ready for surgical suturing.

The needle may be installed in the needle support in principle in two ways: 1. The needle held by the insertion device is movable with the pivotable leg of the insertion device on the same path, which the needle follows when later installed in the suturing apparatus. 2. A slight displacement of the needle during movement of the leg of the insertion device has to be taken into consideration in order to accurately insert the needle into the support of the suturing device.

The invention will be described below in greater detail on the basis of the accompanying drawings.

BRIEF DESCRIPTION OF THE DRAWINGS

FIG. 4 shows a package including a needle with a thread attached to the needle, FIGS. 5a and 5b are top and bottom views of the package, FIG. 7 is a top view of the device as shown in FIG. 6.

DESCRIPTION OF A PREFERRED EMBODIMENT

Figure 1:
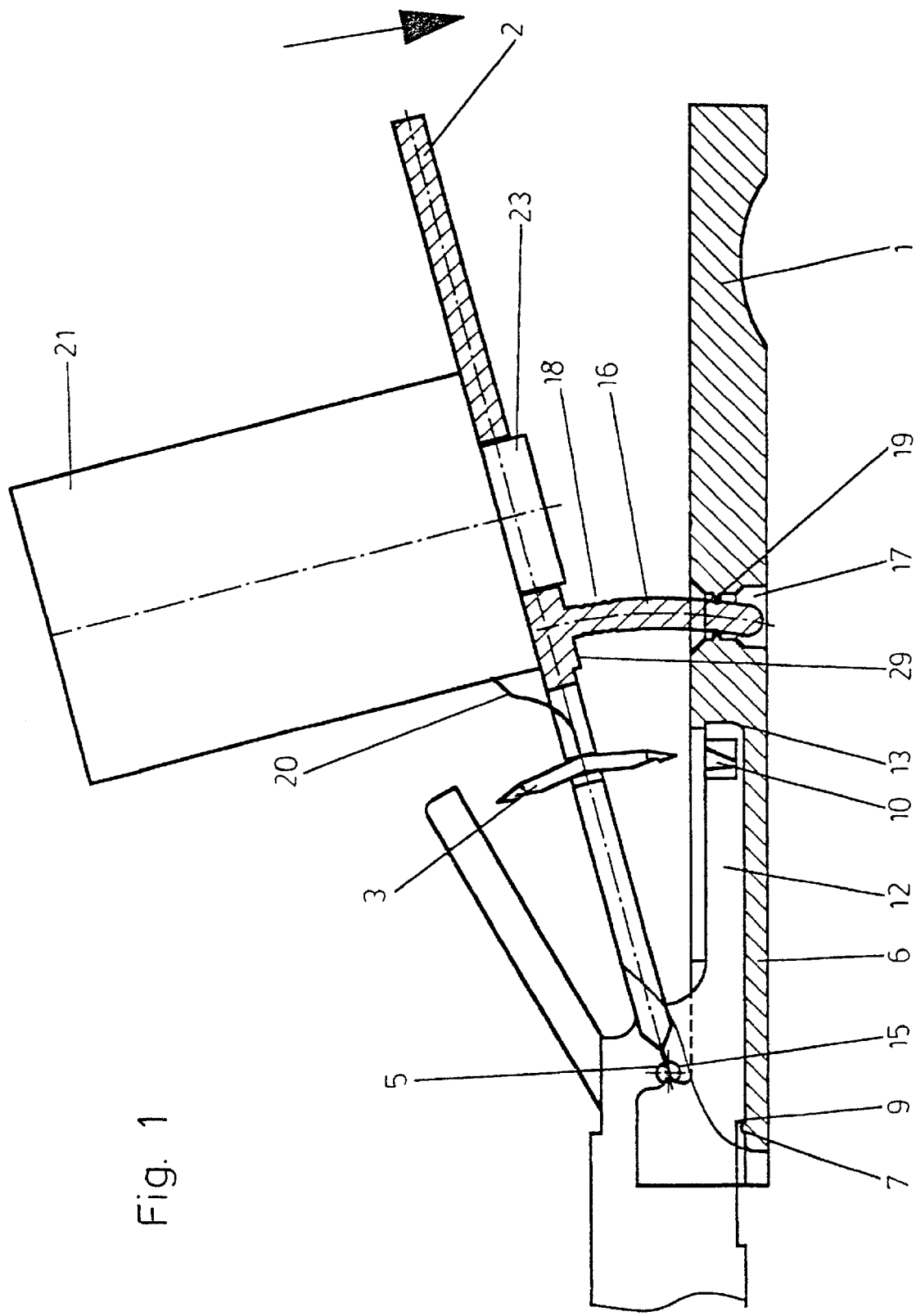
FIG. 1 is a cross-sectional view of the needle insertion device according to the invention.

The needle insertion device as shown in FIG. 1 comprises two leg parts 1 and 2, which are joined by a pivot joint 5, which is preferably a flexible web. The leg part 1, which at its rearward end is adapted in shape to the head of a suturing apparatus, has at its inner side a recess into which a jaw 12 of the suturing apparatus is inserted. When the leg part 1 is slipped onto the jaw 12, the front end of the jaw 12 abuts the end of the recess 13. The cover plate 6 includes a knub 7, which snaps into a recess 9 of the suturing jaw 12, whereby the needle inserting device is properly positioned on the head of the suturing apparatus. The axis of the pivot joint 5 is then disposed on the axis of the bolt or bearing pin 15 around which the movable jaw of the suturing apparatus pivots and the needle 3 which is held on the leg part 2 is disposed in the path of the movement of the needle between the jaws of the suturing apparatus. Therefore, upon movement of the leg part 2 around the pivot joint 5, the needle 3 enters the needle support 10 of the jaw 12 in its proper position in the suturing apparatus.

The needle 3 is retained in the cavity 4 of a pair of tongues 11 of the jaw 12. The thread 20 is firmly attached to the needle 3. It is spooled up in the packaging 21, which is mounted onto the leg part 2 by insertion of the lip 23 into the slot 22 in the leg part 2 of the needle insertion device.

FIG. 1 shows the arrangement in cross-section. For the insertion of the needle 3 into the suturing apparatus, the needle support 10 must be open. First, the leg part 2 of the needle insertion device is moved toward the leg part 1. During this movement, the guide pin 16 enters the guide bore 17, which is conical at both ends. The guide pin 16 is provided with serrations 18, which move along the edge 19 of the bore 17 so that the leg part 2 is retained in a particular position and also in its end position when the stop 29 abuts the leg part 1. At the same time, the needle 3, which is engaged in the leg part 2, is inserted into the open needle support 10. The stop 29 is so selected that the needle must be slightly displaced in its support cavity 4 to make sure that it fully enters the needle support 10. Then a switch-over mechanism in the suturing apparatus is actuated whereby the needle is firmly engaged in the needle support 10. Upon operation of the handle of the suturing apparatus, the movable jaw of the suturing device is then moved toward the stationary jaw so that the needle enters the needle support of the movable jaw and the suturing apparatus jaws are closed. Then the needle insertion device is pulled from the suturing apparatus jaws whereby the needle is disengaged from the cavity 4 as the tongues 11 flex outwardly. At the same time, the thread 20 is pulled out of the packaging 21. The suturing device is then ready for use.

Figure 2:
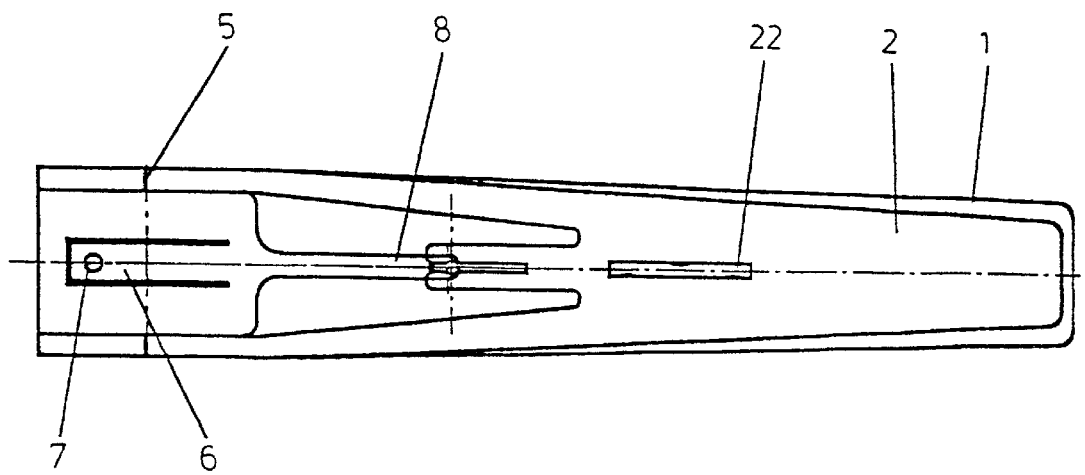
FIG. 2 is a top view of the needle insertion device.
Figure 3:
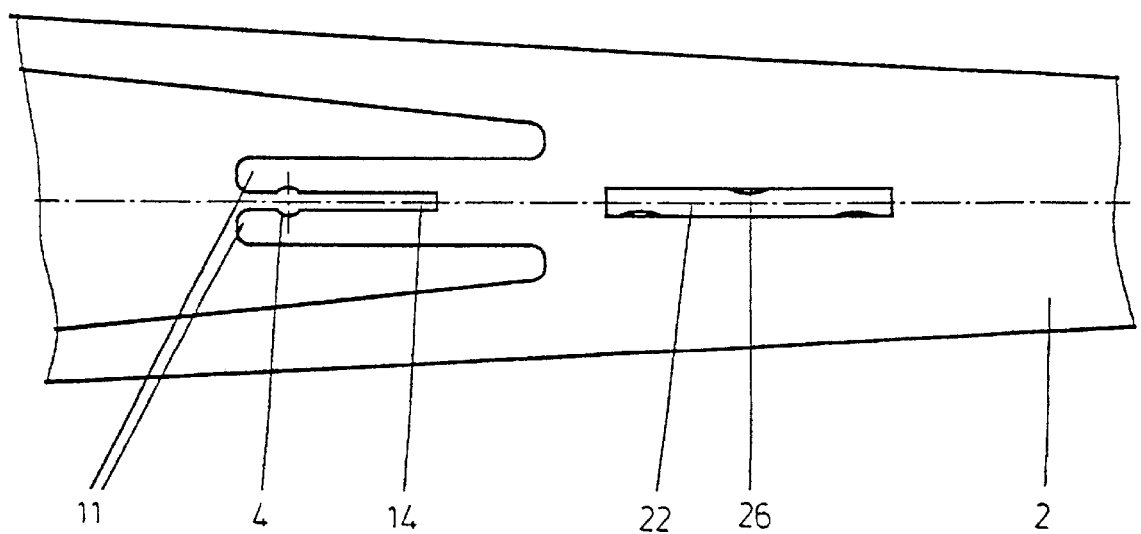
FIG. 3 is an enlarged detail view.

FIG. 2 is a top view of a needle insertion device and FIG. 3 shows, in a partial top view, the needle engagement structure, particularly the needle engagement structure including the cavity 4 formed between the flexible tongues 11. The clamping force of the tongues 11 is determined by the size of the cavity 4 relative to the needle diameter and by the elasticity of the tongues 11 which depends on the length of the slot 14. FIG. 4, 5a and 5b show the packaging 21 for the thread in a folded cardboard container which is held closed by the tongues 24 extending through the cutouts 25. The cardboard container 21 contains the thread 21, which is wound up within the container and extends from the bottom of the container to the needle 3 to which it is firmly tightened. The lip 23 at the bottom edge of the container 21 is inserted into the slot 22. The container 21 may be so designed that only one of its side walls has a lip 23 or each of the side walls has a lip 23, which are then both inserted into the slot 22. For firmly holding the lips 23 in the slot 22, the side walls of the slot 22 are provided with thimbles 26 by which the container lips 23 are bent so as to improve engagement of the lips 23 in the slot 22.

In FIG. 4, the container is shown with a lip 23 into which recesses are cut from opposite ends thereof. The recesses form at the end of the lip 23 bendable tongues 28. These tongues 28 are bent outwardly so that, after insertion of the lip 23 through the slot 22, they snap outwardly whereby the container 21 is locked in its position on the leg part 2.

The needle insertion device is useable, in principle, also for a suturing apparatus with two movable jaws as shown in DE 44 23 881 C1. The needle insertion device is slipped onto one of the two jaws. The insertion device is then so designed that the knub 7 snaps into a recess formed into the respective jaw. Again, the insertion device is so far moved onto the jaw that the joint 5 coincides with the pivot axis of the jaws in order to obtain an accurate needle movement into the needle support 10.

Figure 6:
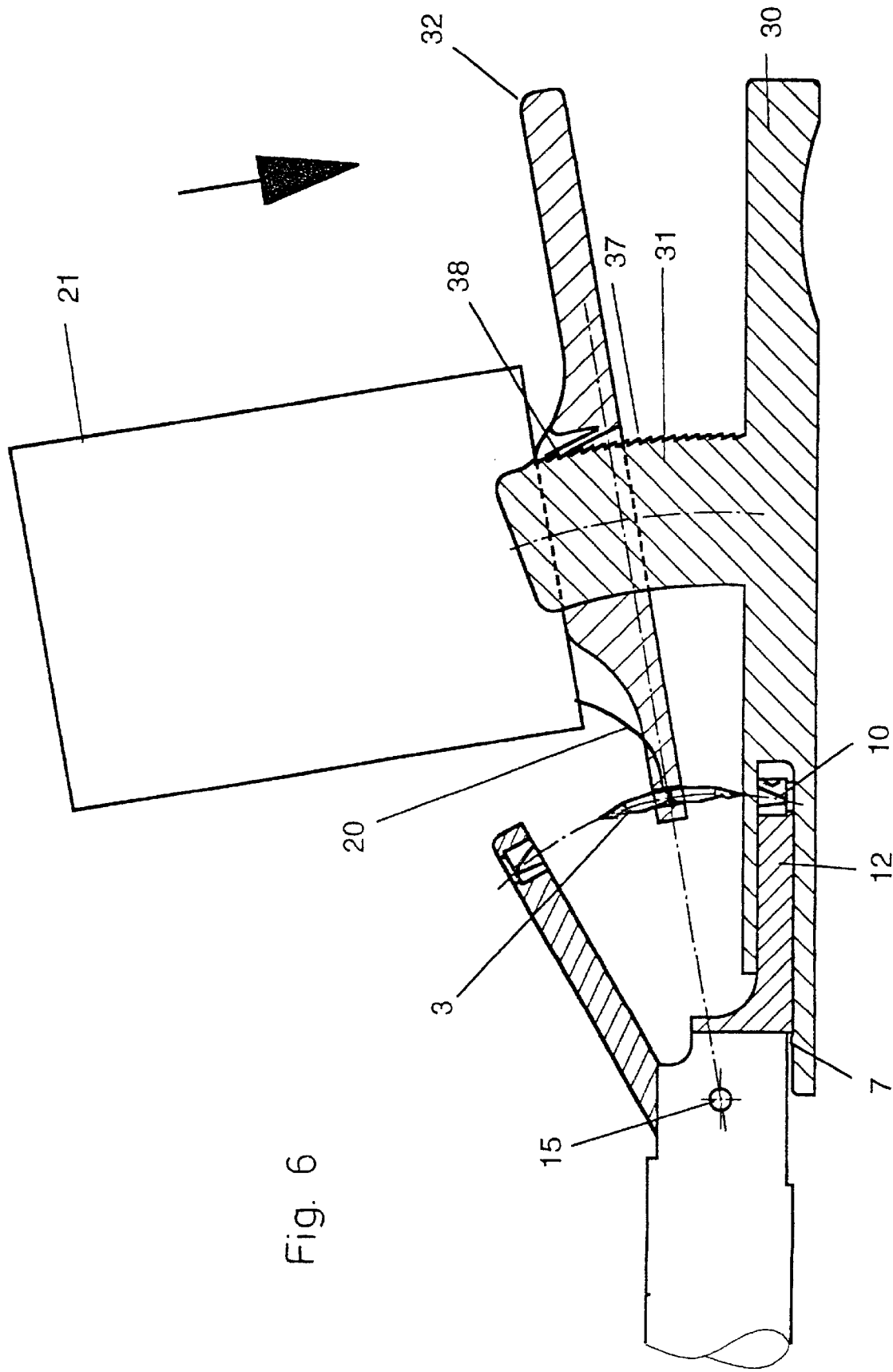
FIG. 6 is a cross-sectional view of a needle insertion device with a curved column.

In another embodiment wherein the needle is also moved about the axis 15 of the suturing apparatus jaws (see FIG. 6), a leg part 30 is slipped onto the jaw 12 of the suturing apparatus and is fixed in position on the jaw 12 by the knub 7 snapping into a recess as described above. The other leg part 32 of the needle insertion device which holds the needle 3 with the thread 20 and the packaging or container 21 is not supported by way of a joint but by one or two columns 31 which extend normally from the leg part 30 and are curved along a circular line having a center of curvature coinciding with the axis 15. The column 31 is provided at one side with serrations 37 and a spring pawl 38, which engages the serrated side of the column 31 ensures that the leg part is held in engagement with the column 31 in any position. The leg part 32 is so designed that, when it is in contact with the leg part 30, the needle is fully inserted into the needle support 10.

In another embodiment, the columns may be straight representing a secant of the arc represented by the curved column. It is also possible to provide a column which extend normally from the leg part 30, but it must be so arranged that the needle 3 still enters accurately the needle support 10 of the jaw 12. The columns are preferably rectangular in cross-section with rounded edges and are formed together with the part 32 in such a way that, when pressed toward the leg part 30, the leg part 32 moves along the columns 31 in a smooth manner and is not held in place by self-locking. The needle installation procedure is the same as already described for the first embodiment.

Preferably, the surgical needle insertion device is a plastic structure made by injection molding. However, it may also consist of pressed cardboard material.

What is claimed is:

1. A device for inserting a surgical suture needle into an endoscopic suture apparatus having jaws with needle supports in which a surgical suturing needle is retained, said device comprising: two legs supported so as to be movable relative to each other, one of said legs having a pin projecting therefrom toward the other leg and the other leg having, an opening receiving said pin so as to provide guidance for the movement of said two legs relative to each other, one of said legs further having a front end including means for receiving a jaw of an endoscopic suturing apparatus, and the other leg having needle engagement means for holding said surgical needle in a predetermined position such that one needle tip enters said needle support in said surgical suturing apparatus jaw when said other leg holding said needle is moved toward said one leg, when said one leg is slipped onto said surgical suturing apparatus jaw.

2. A device according to claim 1, wherein said other leg having said needle engagement means also includes means for mounting a thread packaging onto said other leg.

3. A device according to claim 1, wherein said needle engagement means includes two flexible spring-like tongues defining therebetween a cavity adapted in shape to said suturing needle for receiving and engaging said suturing needle.

4. A device according to claim 1, wherein one of said legs includes a stop structure for limiting movement of said legs toward each other and said pin has a serrated side wall and said guide bore has an edge in contact with said serrated side wall for holding said pin and legs in a given position relative to each other.

5. A device according to claim 2, wherein said other leg includes a slot for receiving lips of said packaging, said slot having side walls with thimbles projecting from opposite sides into said slot for engaging said lips and retaining said packaging on said other legs.

6. A device according to claim 1, wherein said one leg includes a knub projecting therefrom and being received in a recess of said jaw when said one leg is slipped onto, and properly positioned on, said jaw.

7. A device according to claim 6, wherein, with a suturing apparatus having a stationary and a movable jaw, said one leg is adapted to be slipped onto said stationary jaw.

8. A device according to claim 5, wherein said thread is attached to said needle and is pulled from said packaging when, after installation of said needle in said suturing apparatus, said needle insertion device is removed from said suturing apparatus.

9. A device according to claim 1, wherein said two legs are pivotally joined by a flexible web.

10. A device according to claim 9, wherein said surgical needle insertion device is a plastic structure made by injection molding.

11. A device according to claim 9, wherein said surgical needle insertion device consists of cardboard material.

12. A device according to claim 1, wherein said other leg holding said needle is guided by at least one column curved along a circular line having a center of curvature coinciding with the pivot point of the jaws of said surgical suturing apparatus when said one leg is mounted onto one of said jaws.

13. A device according to claim 1, wherein said other leg holding said needle is guided by at least one column extending from said one leg along a secant of a circle having a center point coinciding with the pivot point of the jaws of said surgical suturing apparatus when the other leg is mounted onto one of said jaws.

14. A device according to claim 1, wherein said other leg holding said needle is guided by at least one column which extends normally from said one leg and which guides said other leg such that a needle held by said other leg is moved into said needle support when said one leg is slipped onto one of said jaws and said other leg is moved toward said one leg as guided by said column.

15. A device according to claim 1, wherein said other leg holding said needle is guided by at least one column extending from said one leg and guiding said other leg such that a needle held by said other leg is moved into said needle support when said one leg is slipped onto one of said jaws of said suturing apparatus and said other leg is moved toward said one leg guided by said at least one column, said at least one column including a serrated side wall, and said other leg having a latch engaging said serrated side wall for holding said other leg in position relative to said one leg.

* * * * *